US012733889B2

(12) United States Patent
Wang et al.

(10) Patent No.: US 12,733,889 B2
(45) Date of Patent: Sep. 15, 2026

(54) MEDICAL DEVICE AND MOVEMENT CONTROL METHOD THEREFOR

(71) Applicant: GE Precision Healthcare LLC, Waukesha, WI (US)

(72) Inventors: Kai Wang, Beijing (CN); Xianbo Piao, Beijing (CN); Wenjing Hou, Beijing (CN); Wei Li, Beijing (CN); Wenwen Xiu, Beijing (CN)

(73) Assignee: GE Precision Healthcare LLC, Waukesha, WI (US)

( * ) Notice: Subject to any disclaimer, the term of this patent is extended or adjusted under 35 U.S.C. 154(b) by 189 days.

(21) Appl. No.: 18/593,734

(22) Filed: Mar. 1, 2024

(65) Prior Publication Data

US 2024/0293092 A1 Sep. 5, 2024

(30) Foreign Application Priority Data

Mar. 3, 2023 (CN) ......................... 202310217746.7

(51) Int. Cl.
*A61B 6/04* (2006.01)

(52) U.S. Cl.
CPC .......... *A61B 6/0487* (2020.08); *A61B 6/0407* (2013.01)

(58) Field of Classification Search
CPC ....... A61B 6/035; A61B 5/704; A61B 6/0487; A61B 6/0407; A61B 6/032; A61B 6/467; A61B 6/488; A61B 5/055; A61B 5/70; A61B 5/706
See application file for complete search history.

(56) References Cited

U.S. PATENT DOCUMENTS

| | | | | | |
|---|---|---|---|---|---|
| 4,629,989 | A * | 12/1986 | Riehl | A61B 5/055 | 324/318 |
| 5,474,069 | A * | 12/1995 | Wong | G01R 33/385 | 324/318 |
| 10,080,534 | B2 * | 9/2018 | Yamagata | A61B 5/704 | |
| 2008/0177171 | A1 * | 7/2008 | Francesangeli | A61B 5/055 | 378/20 |
| 2013/0165767 | A1 * | 6/2013 | Darrow | A61B 90/39 | 600/414 |
| 2015/0078514 | A1 * | 3/2015 | Pettinato | A61B 6/503 | 378/20 |
| 2016/0091583 | A1 * | 3/2016 | Saybasili | G01R 33/543 | 600/411 |
| 2024/0293092 | A1 * | 9/2024 | Wang | A61B 6/032 | |

FOREIGN PATENT DOCUMENTS

| | | | | |
|---|---|---|---|---|
| CN | 107257658 B | * 5/2022 | A61B 5/055 |
| CN | 115474951 A | * 12/2022 | A61B 6/5264 |

* cited by examiner

*Primary Examiner* — Oommen Jacob
(74) *Attorney, Agent, or Firm* — Fletcher Yoder, P.C.

(57) ABSTRACT

A medical device and a movement control method therefor is presented. The method includes: determining and storing first distances of movement of a table corresponding to different examination sites, wherein the different examination sites are triggered by different first trigger modes, so that the table is then moved by the corresponding first distances.

17 Claims, 4 Drawing Sheets

401

When an initial scan is performed for each examination site among different examination sites, control the table to be moved by a second distance, so that a center position of a local coil of the medical device corresponding to the examination site is aligned with a positioning light of the medical device

402

Determine the first distance according to the second distance

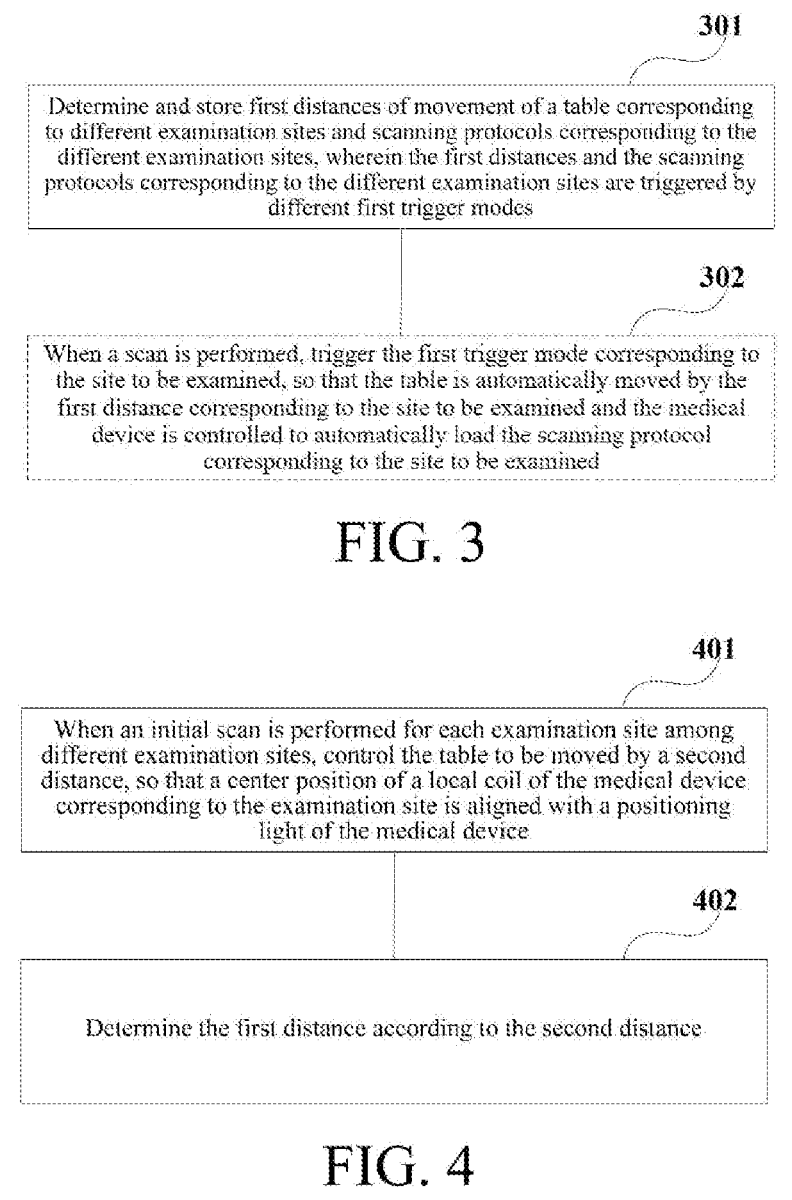

Determine and store first distances of movement of a table corresponding to different examination sites and scanning protocols corresponding to the different examination sites, wherein the first distances and the scanning protocols corresponding to the different examination sites are triggered by different first trigger modes

302

When a scan is performed, trigger the first trigger mode corresponding to the site to be examined, so that the table is automatically moved by the first distance corresponding to the site to be examined and the medical device is controlled to automatically load the scanning protocol corresponding to the site to be examined

When an initial scan is performed for each examination site among different examination sites, control the table to be moved by a second distance, so that a center position of a local coil of the medical device corresponding to the examination site is aligned with a positioning light of the medical device

402

Determine the first distance according to the second distance

FIG. 4

MEDICAL DEVICE AND MOVEMENT CONTROL METHOD THEREFOR

CROSS REFERENCE TO RELATED APPLICATIONS

The present application claims priority and benefit of Chinese Patent Application No. 202310217746.7 filed on Mar. 3, 2023, which is incorporated herein by reference in its entirety.

TECHNICAL FIELD

Embodiments of the present application relate to the technical field of medical devices, and in particular, to a medical device and a movement control method therefor.

BACKGROUND

When a magnetic resonance system is used to scan a patient, it is necessary to position a site to be examined (or region of interest) of the patient at a scanning center of a magnet of the magnetic resonance system. Typically, the patient to be scanned is placed on a table, and the table is then controlled to move so that the patient on the table and a coil are moved to the scanning center of the magnet of the magnetic resonance system for scanning. The table is then moved out after scanning is complete.

Current positioning technology mainly uses a positioning light, that is, a positioning light is provided at the entrance of a magnetic resonance scan space. An operator presses a positioning light key on a control panel and moves a table by means of a table movement key on the control panel. Adjustment is continuously performed until a patient's site to be examined and a coil corresponding to the site to be examined are aligned with the positioning light. A landmark key is pressed. The position of the table when aligned is used as a starting position (for example, a bracket position reads 0). An advance to scan key on the control panel is triggered, so that the table will automatically travel a preset distance and then stop automatically, and the position in which the table stops is exactly so that the patient's site to be examined is located at a scanning center of a magnet of the magnetic resonance system.

SUMMARY

Embodiments of the present application provide a medical device and a movement control method therefor.

According to an aspect of the embodiments of the present application, a movement control method is provided, which is applied to a medical device comprising a movable table, the method comprising: determining and storing first distances of movement of a table corresponding to different examination sites, wherein the different examination sites are triggered by different first trigger modes, so that the table is then moved by the corresponding first distances.

According to an aspect of the embodiments of the present application, a medical device is provided, the medical device comprising: a movable table and a controller; the controller determining and storing first distances of movement of the table corresponding to different examination sites, wherein the different examination sites are triggered by different first trigger modes, so that the table is then moved by the corresponding first distance.

One of the benefits of the embodiments of the present application is that: by pre-storing the first distances of movement of the table corresponding to different examination sites, and different first trigger modes triggering the table to be moved by the corresponding first distances, the scanning process can thus be simplified, and an operator does not need to perform repeated positioning operations, enabling a patient to be quickly and automatically positioned at the scanning center of a medical device, and greatly improving scanning efficiency.

With reference to the following description and drawings, specific implementations of the embodiments of the present application are disclosed in detail, and the means by which the principles of the embodiments of the present application can be employed are illustrated. It should be understood that the implementations of the present application are therefore not limited in scope. Within the scope of the spirit and clauses of the appended claims, the implementations of the present application comprise many changes, modifications, and equivalents.

BRIEF DESCRIPTION OF THE DRAWINGS

The included drawings are used to provide further understanding of the embodiments of the present application, which constitute a part of the description and are used to illustrate the implementations of the present application and explain the principles of the present application together with textual description. Evidently, the drawings in the following description are merely some embodiments of the present application, and a person of ordinary skill in the art may obtain other implementations according to the drawings without involving inventive skill. In the drawings:

FIG. 1 is a schematic diagram of a movement control method according to an embodiment of the present application;

FIG. 2 is a schematic diagram of a first distance determination method according to an embodiment of the present application;

FIG. 3 is a schematic diagram of a movement control method according to an embodiment of the present application;

FIG. 4 is a schematic diagram of a first distance determination method according to an embodiment of the present application;

DETAILED DESCRIPTION

Figure 5:
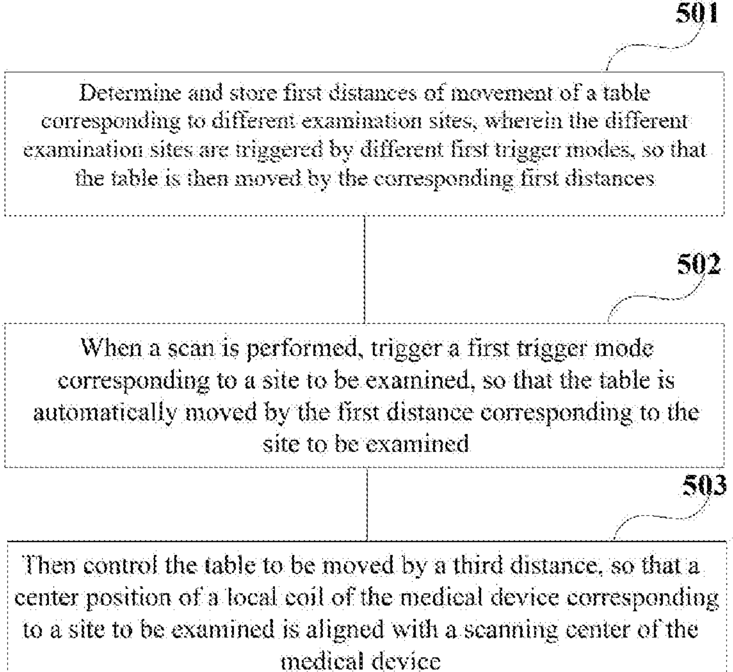
FIG. 5 is a schematic diagram of a movement control method according to an embodiment of the present application.

The foregoing and other features of the embodiments of the present application will become apparent from the following description and with reference to the drawings. In the description and drawings, specific implementations of the present application are disclosed in detail, and part of the implementations in which the principles of the embodiments of the present application may be employed are indicated. It should be understood that the present application is not limited to the described implementations. On the contrary, the embodiments of the present application include all modifications, variations, and equivalents which fall within the scope of the appended claims.

In the embodiments of the present application, the terms "first" and "second" etc., are used to distinguish different elements, but do not represent a spatial arrangement or temporal order, etc., of these elements, and these elements should not be limited by these terms. The term "and/or" includes any and all combinations of one or more associated listed terms. The terms "comprise", "include", "have" etc., refer to the presence of described features, elements, components, or assemblies, but do not exclude the presence or addition of one or more other features, elements, components, or assemblies.

In the embodiments of the present application, the singular forms "a" and "the", etc. include plural forms, and should be broadly construed as "a type of" or "a class of" rather than being limited to the meaning of "one". Furthermore, the term "the" should be construed as including both the singular and plural forms, unless otherwise specified in the context. In addition, the term "according to" should be construed as "at least in part according to . . . " and the term "on the basis of" should be construed as "at least in part on the basis of . . . ", unless otherwise specified in the context.

The features described and/or illustrated for one implementation may be used in one or more other implementations in the same or similar manner, be combined with features in other embodiments, or replace features in other implementations. The term "include/comprise" when used herein refers to the presence of features, integrated components, steps, or assemblies, but does not preclude the presence or addition of one or more other features, integrated components, steps, or assemblies.

Current positioning technology has the following problems: the position of the table needs to be adjusted multiple times to align the patient's site to be examined with the positioning light. Therefore, it takes a long time to adjust the positioning, scanning efficiency is low, and the positioning process is complicated. Even so, positioning deviations may also be caused by manual visual positioning.

Moreover, when a patient goes to the hospital for a body scan, the following scenarios exist: 1) certain hospitals may be specialized hospitals having magnetic resonance scanning devices used only for scanning a particular site. For example, a magnetic resonance device of an orthopedic hospital is mainly used for the scanning of lumbar vertebrae and knee sites; and 2) certain large general hospitals may have multiple magnetic resonance scanning devices, but each magnetic resonance scanning device focuses on scanning a particular site. For example, one magnetic resonance device is mainly used for the scanning of the brain, one magnetic resonance device is mainly used for the scanning of the abdomen, and one magnetic resonance device is mainly used for the scanning of the lumbar vertebrae and knee sites, etc.

Especially in the above scenarios, in view of at least one among the above technical problems, the embodiments of the present application provide a medical device and a movement control method therefor.

The following is a specific description of an embodiment of the present invention with reference to the drawings.

Figures 1, 2:
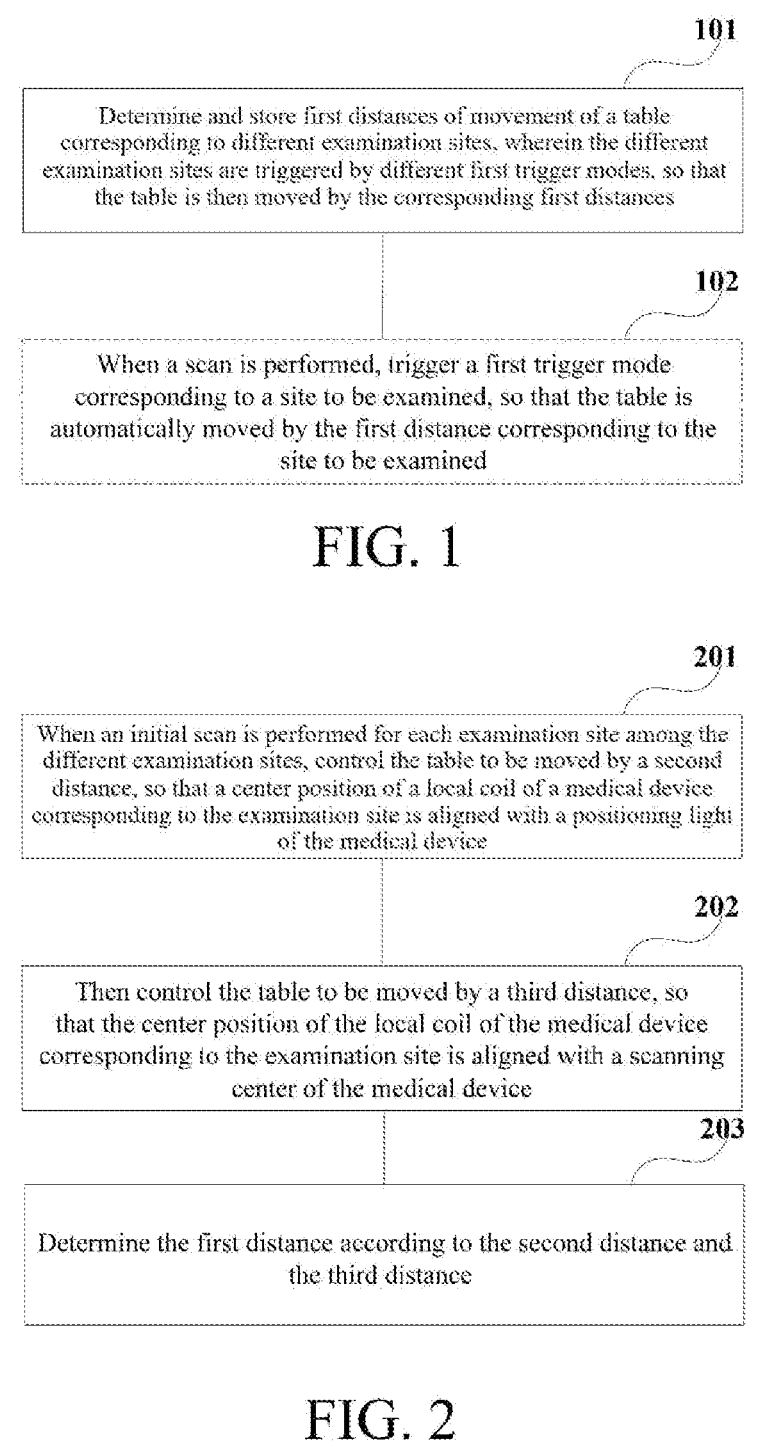

An embodiment of the present application provides a movement control method, which is applied to a medical device. The medical device includes a movable table. The medical device includes at least one among an electronic computed tomography device, a magnetic resonance device, an electron emission tomography device, and a single photon emission computed tomography device, but the present application is not limited thereto. The medical device may also be other devices that can acquire medical images. FIG. 1 is a schematic diagram of a movement control method according to an embodiment of the present application. As shown in FIG. 1, the method includes:

101, determining and storing first distances of movement of a table corresponding to different examination sites, wherein the different examination sites are triggered by different first trigger modes, so that the table is then moved by the corresponding first distances.

In some embodiments, the movable table is used to carry a scan subject, such as a patient, and is configured to be in communication with the entrance of a scanning chamber of a medical device and to move in a horizontal (Z) direction to allow the scan subject thereon to enter and exit the scanning chamber or to travel in the Z direction in the scanning chamber. The movable table can be moved from outside of the scanning chamber to a center position inside of the scanning chamber. The center position may be different based on a site to be examined. For example, the center position may include a magnet center of a magnetic resonance system.

In some embodiments, the medical device further includes a local coil. The local coil includes at least one among a head coil, an abdominal coil, a spinal coil, a thoracic coil, a neck coil, a shoulder coil, and an ankle coil. Different coils are used for scanning examination sites corresponding thereto. For example, the head coil is used for scanning the head, the spinal coil is used for scanning the spine, the abdominal coil is used for scanning the abdomen, and so on. The local coil may be a fixed coil (e.g., a spinal coil or head and neck coils, etc.) or a non-fixed coil (e.g., an abdominal coil, etc.). When the fixed coil is used to scan a scan subject, the fixed coil can be fixed on the table, the scan subject is carried by the table, and the scan subject needs to roughly align the center of the site to be examined thereof with the center of the fixed coil. The non-fixed coil refers to a coil that is not fixed on the table. When the non-fixed coil is used to scan the scan subject, the scan subject is first carried by the table, and then the non-fixed coil is placed in a position in which its center is roughly aligned with the center of the site to be examined.

In some embodiments, the first distance means that: for an examination site of the scan subject, after the table is moved by a first distance corresponding to the examination site from an initial position, the center position of the local coil of the medical device is aligned with a scanning center of the medical device, or the center position of the local coil of the medical device is aligned with a positioning light of the medical device, which will be described separately below.

(I) For the examination site of the scan subject, after the table is moved by a first distance corresponding to the examination site from the initial position, the center position of the local coil of the medical device is aligned with the scanning center of the medical device.

How to determine the first distance is first described below.

FIG. 2 is a schematic diagram of a method for determining the first distance according to an embodiment of the present application. As shown in FIG. 2, the method includes: at step 201, when an initial scan is performed for each examination site among the different examination sites, controlling the table to be moved by a second distance, so that the center position of the local coil of the medical device corresponding to the examination site is aligned with the positioning light of the medical device.

At step 202, controlling the table to be moved by a third distance, so that the center position of the local coil of the medical device corresponding to the examination site is aligned with the scanning center of the medical device; and at step 203, determining the first distance according to the second distance and the third distance.

In some embodiments, the initial scan refers to a body scan performed on any scan subject when using a medical device for the first time, configuring the medical device, or maintaining the medical device, etc. The scan may be a complete scanning imaging process, or the scan may only include a positioning process (i.e., a process of moving a table carrying a scan subject into a scanning chamber), the process of determining the first distance is similar to the positioning process in the related art. In 201-203, for an examination site A, the scan subject is placed on the table, and the examination site A is aligned with the center of the corresponding local coil. An operator presses a positioning light key on a control panel and moves the table by means of a table movement key on the control panel. Adjustment is continuously performed until the center of the local coil corresponding to the examination site is aligned with the positioning light. The distance between the initial position of the table to the position of the table when aligned with the positioning light is used as the second distance. A landmark key is pressed. The position of the table when aligned with the positioning light is used as a first starting position (that is, a bracket position reads 0). An advance to scan key on the control panel is triggered, so that the table will automatically travel a preset distance from the first starting position and then stop automatically. At this time, the center position of the local coil corresponding to the examination site A is aligned with the scanning center of the medical device. The distance between the first starting position and the stop position of the table is used as the third distance. Therefore, the distance of the table from the initial position to the stop position is a first distance DA corresponding to the examination site A. The first distance is determined according to the second distance and the third distance, that is, the first distance is equal to the sum of the second distance and the third distance. For other examination sites B, the above process is repeated to separately determine a first distance DB corresponding to each examination site B.

In some embodiments, after the first distance corresponding to each examination site is determined, the first distance needs to be stored. The first distance may be stored in a memory of the medical device. In order to improve the convenience of operation, the first distances corresponding to different examination sites are triggered and stored by different second trigger modes. A trigger medium in each second trigger mode includes physical keys on the medical device, virtual keys on a user interface of the medical device, or voice commands received by a microphone array. Different second trigger modes include: different physical keys, different virtual keys, different key pressing means, different voice commands, or different numbers of keys. The first distance DA corresponding to the examination site A and a second distance DB corresponding to an examination site B are illustrated below as examples.

In some embodiments, the trigger mediums in the second trigger modes is a physical key of the medical device. The physical key may be provided at any location of the medical device, for example, on a table, on a magnet housing of the medical device, on a control panel of an operating room, or the like. The trigger means of the physical key includes pressing, turning a knob, and the like. The physical key may also have an illuminating or buzzing effect or the like to prompt that the physical key is triggered. The embodiments of the present application are not limited thereto.

For example, the first distances corresponding to different examination sites are stored by triggering different physical keys. The storage of the first distance DA into the memory is triggered by pressing a physical key SETA, and the storage of the second distance DB into the memory is triggered by pressing a physical key SETB.

For example, the first distances corresponding to different examination sites are triggered and stored by different key pressing means of the same physical key. For example, the storage of the first distance DA into the memory is triggered by short-pressing a physical key SET, and the storage of the second distance DB into the memory is triggered by long-pressing the physical key SET. Alternatively, the storage of the first distance DA into the memory is triggered by rotating the physical key SET clockwise, and the storage of the second distance DB into the memory is triggered by rotating the physical key SET counterclockwise.

For example, the first distances corresponding to different examination sites are stored by triggering different physical key combinations. For example, the storage of the first distance DA into the memory is triggered by pressing the physical key SET+a physical key 1, and the storage of the second distance DB into the memory is triggered by pressing the physical key SET+a physical key 2, wherein the physical key SET and other physical keys may be pressed simultaneously or successively. The embodiments of the present application are not limited thereto. For example, when the first distance needs to be stored, the physical key SET may be pressed to enter a storage mode (illuminating or buzzing prompts to continue pressing other keys). If the physical key 1 is pressed, the first distance DA is stored. If the physical key 2 is pressed, the second distance DB is stored.

For example, the first distances corresponding to different examination sites are stored by triggering different numbers of physical keys. For example, the storage of the first distance DA into the memory is triggered by pressing the physical key SET, and the storage of the second distance DB into the memory is triggered by pressing at the same time the physical key SET+the physical key 2.

The above physical keys (e.g., the physical key SET, the physical key 1, and the physical key 2) are newly added keys of the medical device, but the embodiments of the present application are not limited thereto. For example, the above physical keys may be existing function keys of the medical device or combinations of the existing function keys. Therefore, there is no need to re-design and update the medical device hardware, thereby saving costs.

In some embodiments, the trigger mediums in the second trigger modes are virtual keys of the medical device. The virtual keys may be provided on a user interface of a display of the medical device. The trigger means of the virtual keys includes clicking an input device, clicking a touch screen, or the like.

For example, the first distances corresponding to different examination sites are stored by triggering different virtual keys. The storage of the first distance DA into the memory is triggered by clicking a virtual key SETA, and the storage of the second distance DB into the memory is triggered by clicking a virtual key SETB.

For example, the first distances corresponding to different examination sites are triggered and stored by different key pressing means of the same virtual key. For example, the storage of the first distance DA into the memory is triggered by single-clicking a virtual key SET, and the storage of the second distance DB into the memory is triggered by double-clicking the virtual key SET.

For example, the first distances corresponding to different examination sites are stored by triggering different virtual key combinations. For example, the storage of the first distance DA into the memory is triggered by clicking the virtual key SET+a virtual key 1, and the storage of the second distance DB into the memory is triggered by clicking the virtual key SET+a virtual key 2, wherein the virtual key SET and other virtual keys may be clicked simultaneously or successively. The embodiments of the present application are not limited thereto. For example, when the first distance needs to be stored, the virtual key SET may be clicked to enter a storage mode. If the virtual key 1 is clicked again, the first distance DA is stored. If the virtual key 2 is clicked again, the second distance DB is stored.

For example, the first distances corresponding to different examination sites are stored by triggering different numbers of virtual keys. The storage of the first distance DA into the memory is triggered by clicking a virtual key SET, and the storage of the second distance DB into the memory is triggered by clicking at the same time the virtual key SET+the virtual key 2.

In some embodiments, the trigger mediums in the second trigger modes are voice commands received by a microphone array. The microphone array may be provided at any location of the medical device, such as on the table, on a scanning unit, on a control panel, etc. The embodiments of the present application are not limited thereto.

For example, the first distances corresponding to different examination sites are stored by triggering different voice commands. For example, the storage of the first distance DA into the memory is triggered by means of voice command "store examination site A", and the storage of the second distance DB into the memory is triggered by means of voice command "store examination site B". However, the embodiments of the present application are not limited thereto.

In some embodiments, considering the foregoing scanning scenarios, each medical device may focus on scanning a specific site. Therefore, for each medical device, it is not necessary to determine and store first distances for all examination sites (corresponding coils) of a scan subject. For example, for a medical device A, the first distance corresponding to the head and the first distance corresponding to the neck are determined, and for a medical device B, the first distance corresponding to the knee and the first distance corresponding to the ankle joint are determined, and so on. The first distances of movement of a table corresponding to the examination sites that are specifically determined may be determined as needed, and the embodiments of the present application are not limited thereto.

In some embodiments, after the storage (memorization) of the first distance corresponding to each examination site is completed, the method further includes: at step 102, when a scan is performed, triggering a first trigger mode corresponding to a site to be examined, so that the table is automatically moved by the first distance corresponding to the site to be examined.

In some embodiments, the different examination sites are triggered by different first trigger modes, so that the table is then moved by the corresponding first distances.

In some embodiments, during scanning, the first distances corresponding to different examination sites are triggered by different first trigger modes, and the table is triggered by the first trigger modes to be automatically moved by the corresponding first distances, so that the center position of the local coil is aligned with the scanning center of the medical device, thereby simplifying the scanning process. There is no need to adjust the position of the table multiple times or to position the positioning light, enabling the scan subject to be quickly and automatically positioned at the scanning center of the medical device.

In some embodiments, the trigger medium in each first trigger mode includes a physical key on the medical device, a virtual key on the user interface of the medical device, or a voice command received by the microphone array. The different first trigger modes include: different physical keys, different virtual keys, different key pressing means, different voice commands, or different numbers of keys, which are illustrated in the following examples.

In some embodiments, the trigger medium in the first trigger mode is a physical key of the medical device. The physical key may be provided at any position of the medical device, such as on the table, on the scanning unit, on the control panel, etc. The trigger means of the physical key includes pressing, turning a knob, etc. The physical key may also have an illuminating or buzzing effect or the like to prompt that the physical key is triggered. The embodiments of the present application are not limited thereto. The table is triggered by the physical key to be moved by the corresponding first distance, so that a positioning operation can be automatically achieved using "one key".

For example, the table is moved by the first distances after different physical keys are triggered. When the examination site A is scanned, the table is triggered to be moved by a first distance DA by pressing a physical key ADVANCE1. When the examination site B is scanned, the table is triggered to be moved by a first distance DB by pressing a physical key ADVANCE2.

For example, the table is triggered by different key pressing means of the same physical key to be moved by the first distances. For example, when the examination site A is scanned, the table is triggered to be moved by the first distance DA by short-pressing (or rotating clockwise) the physical key ADVANCE. When the examination site B is scanned, the table is triggered to be moved by the first distance DB by long-pressing (or rotating counterclockwise) the physical key ADVANCE.

For example, the table is moved by the first distances after different physical key combinations are triggered. For example, the table is triggered to be moved by the first distance DA by pressing the physical key ADVANCE+the physical key 1, and the table is triggered to be moved by the first distance DB by pressing the physical key ADVANCE+ the physical key 2, wherein the above key combinations may be pressed simultaneously or successively. The embodiments of the present application are not limited thereto. For example, when needing to move by the first distance, the physical key ADVANCE may be pressed to enter an advance mode (illuminating or buzzing prompts to continue pressing other keys). If the physical key 1 is pressed, the table is moved by the first distance DA. If the physical key 2 is pressed, the table is moved by the second distance DB.

For example, the table is moved by the first distances after different numbers of physical keys are triggered. For example, the table is triggered to be moved by the first distance DA by pressing the physical key ADVANCE, and the table is triggered to be moved by the first distance DB by pressing at the same time the physical key ADVANCE+the physical key 2.

The above physical keys (e.g., the physical key ADVANCE, the physical key 1, and the physical key 2) are newly added keys of the medical device, but the embodiments of the present application are not limited thereto. For example, the above physical keys may be existing function keys of the medical device or combinations of the existing function keys. Therefore, there is no need to re-design and update the medical device hardware, thereby saving costs.

In some embodiments, the trigger medium in the first trigger mode is a virtual key of the medical device. The virtual key may be provided on the user interface of the display of the medical device. The trigger mode of the virtual key includes clicking the input device, clicking the touch screen, or the like. The table is triggered by the virtual key to be moved by the corresponding first distance, so that a positioning operation can be automatically achieved using "one key".

For example, the table is moved by the first distances after different virtual keys are triggered. When the examination site A is scanned, the table is triggered to be moved by the first distance DA by clicking a virtual key ADVANCE1. When the examination site B is scanned, the table is triggered to be moved by the first distance DB by clicking a virtual key ADVANCE2.

For example, the table is triggered by different key pressing means of the same virtual key to be moved by the first distances. For example, when the examination site A is scanned, the table is triggered to be moved by the first distance DA by single-clicking the virtual key ADVANCE. When the examination site B is scanned, the table is triggered to be moved by the first distance DB by double-clicking the virtual key ADVANCE.

For example, the table is moved by the first distances after different virtual key combinations are triggered. For example, the table is triggered to be moved by the first distance DA by clicking the virtual key ADVANCE+the virtual key 1, and the table is triggered to be moved by the first distance DB by clicking the virtual key ADVANCE+the virtual key 2. The embodiments of the present application are not limited thereto. The above key combinations may be clicked simultaneously or successively. For example, when the table needs to be moved by the first distance, the virtual key ADVANCE may be clicked to enter an advance mode (illuminating or buzzing prompts to continue pressing other keys). If the virtual key 1 is clicked, the table is moved by the first distance DA. If the virtual key 2 is clicked, the table is moved by the second distance DB.

For example, the table is moved by the first distances after different numbers of virtual keys are triggered. For example, the table is triggered to be moved by the first distance DA by clicking the virtual key ADVANCE, and the table is triggered to be moved by the first distance DB by clicking at the same time the virtual key ADVANCE+the virtual key 2.

In some embodiments, the trigger medium in the first trigger mode is a voice command received by the microphone array. The microphone array may be provided at any location of the medical device, such as on the table, on a scanning unit, on a control panel, etc. The embodiments of the present application are not limited thereto.

For example, the table is moved by the first distances after different voice commands are triggered. For example, the table is triggered to be moved by the first distance DA by means of the voice command "scan examination site A", and the table is triggered to be moved by the first distance DB by means of the voice command "scan examination site B". However, the embodiments of the present application are not limited thereto.

In some embodiments, the first trigger modes are associated or not associated with the corresponding second trigger modes. The embodiments of the present application are not limited thereto. The first trigger modes corresponding to the second trigger modes means that they are targeted to the same examination site. The first trigger modes being associated with the second trigger modes includes: the first trigger modes and the second trigger modes having at least one identical physical key or virtual key (or at least one keyword in corresponding voice commands being the same), or having the same key pressing means. The first trigger modes not being associated with the second trigger modes includes: the trigger mediums in the first trigger modes and the second trigger modes being different (including different types or different keys, etc.), which is illustrated in the following examples.

For example, the trigger mediums of the first trigger modes are physical keys or virtual keys, and the trigger mediums of the second trigger modes are voice commands. The specific trigger means are as described previously, and vice versa. Then, the first trigger modes are not associated with the second trigger modes.

For example, the trigger mediums of the first trigger modes are physical (or virtual) keys SETA and SETB, and the trigger mediums of the second trigger modes are physical (or virtual) keys ADVANCE1 and ADVANCE2. The specific trigger means are as described previously, and vice versa. Then, the first trigger modes are not associated with the second trigger modes.

For example, the trigger mediums of the first trigger modes and the second trigger modes are physical (or virtual) keys, and the keys used by the first trigger modes and the corresponding second trigger modes have the same physical (or virtual) keys. For example, during the initial scan, for the examination site A, the first distance DA is stored by pressing (clicking) the physical (or virtual) key SET+the physical (or virtual) key 1. During a subsequent scan of the examination site A, by pressing (clicking) the physical key 1, the table is triggered to be moved by the first distance DA. For the examination site B, the first distance DB is stored by pressing (clicking) the physical key SET+the physical key 2. During a subsequent scan of the examination site B, by pressing (clicking) the physical key 2, the table is triggered to be moved by the first distance DB. That is to say, for the examination site A, the first trigger mode and the second trigger mode share the physical key 1, and for the examination site B, both the first trigger mode and the second trigger mode use the physical key 2. That is, the first trigger modes are associated with the corresponding second trigger modes. Therefore, the number of keys can be reduced, and the operation method is simple, facilitating the operator to understand visually.

For example, the trigger mediums of the first trigger modes and the second trigger modes are physical (or virtual) keys (different keys), but the first trigger modes and the corresponding second trigger modes share the same key pressing means. For example, during the initial scan, for the examination site A, the first distance DA is stored by short-pressing (or single-clicking) the physical (or virtual) key SET. During a subsequent scan of the examination site A, by short-pressing (or single-clicking) the physical key ADVANCE, the table is triggered to be moved by the first distance DA. For the examination site B, the first distance DB is stored by long-pressing (or double-clicking) the physical key SET. During a subsequent scan of the examination site B, by long-pressing (or double-clicking) the physical key ADVANCE, the table is triggered to be moved by the first distance DB. That is to say, for the examination site A, the first trigger modes and the second trigger modes share the key pressing means of short-pressing (or single-clicking), and for the examination site B, the first trigger mode and the second trigger mode share the key pressing mode of long-pressing (or double-clicking). That is, the first trigger modes are associated with the corresponding second trigger modes. Therefore, the number of keys can further be reduced.

For example, the trigger mediums of the first trigger modes and the second trigger modes are voice commands, and the first trigger modes and the corresponding second trigger modes share the same keyword. For example, during the initial scan, for the examination site A, the first distance DA is stored by means of the voice command "store examination site A". During a subsequent scan of the examination site A, by means of the voice command "scan examination site A", the table is triggered to be moved by the first distance DA. For the examination site B, the first distance DB is stored by means of the voice command "store examination site B". During a subsequent scan of the examination site B, by means of the voice command "scan examination site B", the table is triggered to be moved by the first distance DB. That is to say, for the examination site A, the first trigger mode and the second trigger mode share the same keyword "examination site A", and for the examination site B, the first trigger mode and the second trigger mode share the same keyword "examination site B". That is, the first trigger modes are associated with the corresponding second trigger modes.

FIG. 3 is another schematic diagram of a movement control method according to an embodiment of the present application. As shown in FIG. 3, the method includes: at step 301, determining and storing first distances of movement of a table corresponding to different examination sites and scanning protocols corresponding to the different examination sites, wherein the first distances and the scanning protocols corresponding to the different examination sites are triggered by different first trigger modes.

At step 302, when a scan is performed, triggering a first trigger mode corresponding to a site to be examined, so that the table is automatically moved by the first distance corresponding to the site to be examined and the medical device is controlled to automatically load the scanning protocol corresponding to the site to be examined.

The same content regarding 301-302 as the above will not be described again, and the differences are described below.

In existing methods, after the table is moved to the scanning chamber, the operator can select, on an operation interface, a scanning protocol (abdominal protocol, head protocol, etc.) corresponding to the examination site. The scanning protocol includes a preset scanning parameter, etc. Then, scanning of the examination site is started. In order to further simplify the scanning process, in the embodiment of the present application, in addition to determining and storing the first distances corresponding to different examination sites, in 301, scanning protocols corresponding to the different examination sites may further be determined and stored, wherein a scanning protocol corresponding to an examination site may be determined according to the operator's selection, and the scanning protocol corresponding to the examination site is stored in the memory of the medical device. The scanning protocol and the first distance corresponding to the examination site may also be triggered and stored by the foregoing corresponding second trigger mode. For example, the storage of the first distance DA and scanning protocol PA into the memory is triggered by pressing the physical key SET+physical key 1, and the storage of the second distance DB and scanning protocol PB into the memory is triggered by pressing the physical key SET+physical key 2. For other implementations in which the storage of the scanning protocol is triggered by the second trigger mode, please refer to the foregoing example in which the storage of the first distance is triggered by the second trigger mode, which will not be described again here. When a scan is performed in 302, upon triggering a first trigger mode corresponding to a site to be examined, in addition to automatically moving the table by a first distance corresponding to the site to be examined, it is also possible to control the medical device to automatically load a scanning protocol corresponding to the site to be examined. That is, the scanning protocol and the first distance corresponding to the examination site may simultaneously be triggered by the foregoing corresponding first trigger mode to load and move. For example, by pressing the physical key 1, the table is triggered to be moved by the first distance DA, and the scanning protocol corresponding to the examination site A is automatically loaded, and by pressing the physical key 2, the table is triggered to be moved by the second distance DB, and the scanning protocol corresponding to the examination site B is automatically loaded. With regard to other examples of triggering in the first trigger mode, no more examples are given here.

In some embodiments, in 102, after the table is moved by the first distance, the scanning protocol may be manually selected (adjusting a scanning parameter), and a scanning imaging process is started. Alternatively, in 302, after the table is moved by the first distance and the scanning protocol is automatically loaded (using a preset scanning parameter), the scanning imaging process is automatically triggered, thereby further simplifying the scanning process.

(II) For the examination site of the scan subject, after the table is moved from the initial position by the first distance corresponding to the examination site, the center position of the local coil of the medical device is aligned with the positioning light of the medical device.

How to determine the first distance is first described below.

FIG. 4 is a schematic diagram of a method for determining the first distance according to an embodiment of the present application. As shown in FIG. 4, the method includes: at step 401, when an initial scan is performed for each examination site among the different examination sites, controlling the table to be moved by a second distance, so that the center position of the local coil of the medical device corresponding to the examination site is aligned with the positioning light of the medical device; and at step 402, determining the first distance according to the second distance.

In some embodiments, for a method for determining the second distance, reference may be made to step 201 described previously, which will not be described again here. The first distance is equal to the second distance.

In some embodiments, after the first distance corresponding to each examination site is determined, the first distance needs to be stored. The first distance may be stored in the memory of the medical device. The first distances corresponding to different examination sites are triggered and stored by different second trigger modes. Regarding the triggering and storage by each second trigger mode, reference is made to the implementation in (I), which will not be described again here.

FIG. 5 is another schematic diagram of a movement control method according to an embodiment of the present application. As shown in FIG. 5, the method includes: at step 501, determining and storing first distances of movement of a table corresponding to different examination sites, wherein the different examination sites are triggered by different first trigger modes, so that the table is then moved by the corresponding first distances.

At step 502, when a scan is performed, triggering a first trigger mode corresponding to a site to be examined, so that the table is automatically moved by the first distance corresponding to the site to be examined; and at step 503, then controlling the table to be moved by a third distance, so that the center position of the local coil of the medical device corresponding to the examination site is aligned with the scanning center of the medical device.

In some embodiments, during scanning, the first distances corresponding to different examination sites are triggered by different first trigger modes, and the table is triggered by the first trigger modes to be automatically moved by the corresponding first distances, so that the center position of the local coil is aligned with the positioning light of the medical device. Then, the table is controlled to be moved by the third distance, so that the center position of the local coil of the medical device corresponding to the examination site is aligned with the scanning center of the medical device, thereby simplifying the scanning process. That is, there is no need to adjust the position of the table multiple times, enabling the scan subject to be quickly and automatically positioned at the scanning center of the medical device.

In some embodiments, for the implementation of the first trigger modes, reference is made to the implementation in (I), and for the implementation of 502, reference may made to 102, which will not be repeated here. In 503, after the table is moved by the first distance, the landmark key is pressed, and the position of the table when aligned is used as the starting position (that is, the bracket position reads 0). By triggering the advance to scan key on the control panel, the table will be automatically moved by the third distance (the third distance is preset in the medical device) to enter the scanning space and automatically stop after advancing the third distance. The position in which the table stops is exactly so that the patient's site to be examined (the corresponding local coil) is located at the scanning center of the medical device.

In some embodiments, in 501, in addition to determining and storing the first distances corresponding to different examination sites, scanning protocols corresponding to different examination sites may be determined and stored, and the scanning protocols and first distances corresponding to the different examination sites may likewise be triggered and stored by the foregoing corresponding second trigger modes. When a scan is performed in 502, upon triggering a first trigger mode corresponding to a site to be examined, in addition to automatically moving the table by the first distance corresponding to the site to be examined, it is also possible to control the medical device to automatically load the scanning protocol corresponding to the site to be examined. That is, the scanning protocol and the first distance corresponding to the examination site may simultaneously be triggered by the foregoing corresponding first trigger mode to load and move. For details, reference may be made to 301-302, and the repeated parts will not be described again.

In some embodiments, in 503, after the table is moved by the third distance, the scanning protocol may be manually selected (adjusting a scanning parameter), and a scanning imaging process is started. Alternatively, after the scanning protocol is automatically loaded (using a preset scanning parameter) and the table is moved by the third distance, the scanning imaging process is automatically triggered, thereby further simplifying the scanning process.

With the above embodiments, by pre-storing the first distances table movement corresponding to different examination sites and triggering the first distances corresponding to the table movement by different first trigger modes, the scanning process may be simplified, the operator does not need to repeatedly carry out a positioning operation, and the patient may be quickly and automatically positioned at the medical device scanning center, greatly increasing scan efficiency.

Figure 6:
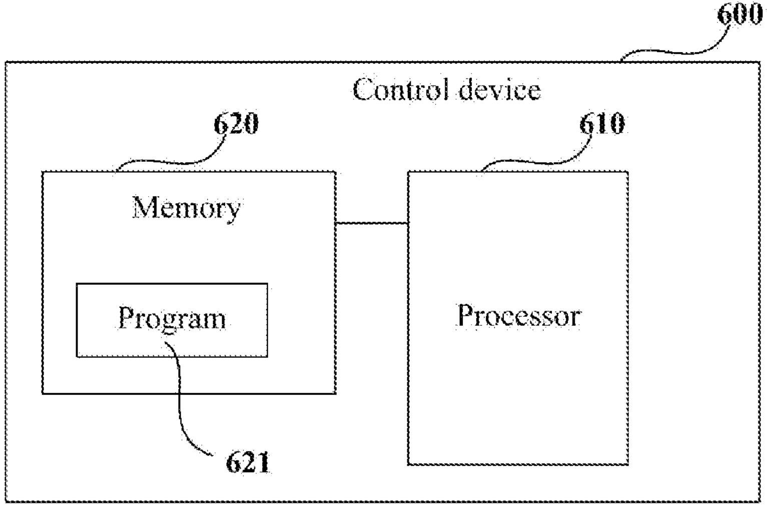
FIG. 6 is a schematic diagram of a control device according to an embodiment of the present application.

The embodiments of the present application further provide a control device. FIG. 6 is a schematic diagram of a control device according to an embodiment of the present application. As shown in FIG. 6, the control device 600 may include: one or more processors (for example, a central processing unit (CPU)) 610, and one or more memories 620. The memory 620 is coupled to the processor 610. The memory 620 can store various types of information, etc. In addition, the memory further inputs a control program 621 of a device, and the program 621 is executed under control of the processor 610. The memory 620 may include, for example, a ROM, a floppy disk, a hard disk, an optical disk, a magneto-optical disk, a CD-ROM, or a non-volatile memory card.

In some embodiments, the processor 610 is configured to determine the first distances of movement of the table corresponding to different examination sites, and the memory 620 stores the corresponding first distances. Alternatively, the processor 610 is configured to determine the first distances of movement of the table corresponding to different examination sites and the scanning protocols corresponding to the different examination sites. The memory 620 stores the corresponding first distances and the corresponding scanning protocols. For the implementations thereof, reference may be made to the foregoing embodiments, which will not be described here again.

It should be noted that the control device 600 does not necessarily include all of the components shown in FIG. 6. In addition, the control device 600 for the input device may further include components not shown in FIG. 6, for which reference may be made to related technologies.

The processor 610 may communicate with a medical device, a display, etc. The processor 610 may also be referred to as a microcontroller unit (MCU), a microprocessor, or a microcontroller, or other processor apparatuses and/or logic apparatuses. The processor 610 may include a reset circuit, a clock circuit, a chip, a microcontroller, etc. The functions of the processor 610 may be integrated on the motherboard of the medical device (e.g., the processor 610 is configured as a chip connected to a central processing unit (CPU) of the motherboard), or may be configured independently of the motherboard. The embodiments of the present application are not limited thereto.

For the sake of simplicity, FIG. 6 only exemplarily shows the connection relationship or signal direction between various components or modules, but it should be apparent to those skilled in the art that various related technologies such as a bus connection can be used. The various components or modules can be implemented by means of a hardware facility such as a processor or a memory, etc. The embodiments of the present application are not limited thereto.

Figure 7:
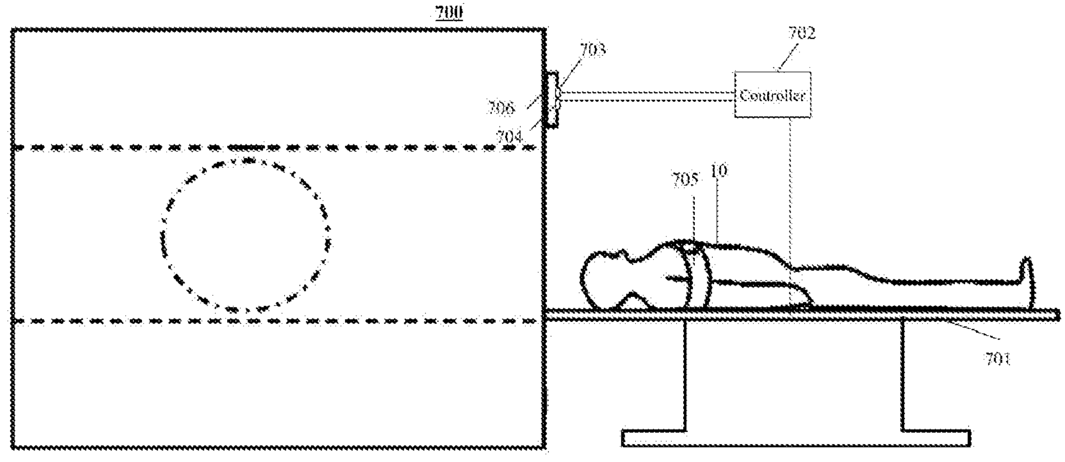
FIG. 7 is a schematic diagram of a medical device according to an embodiment of the present application.

The embodiments of the present application further provide a medical device. FIG. 7 is a schematic diagram of a medical device according to an embodiment of the present application. For example, the medical device may be a computed tomography device, a magnetic resonance device, or the like. As shown in FIG. 7, the medical device 700 includes a movable table 701 and a controller 702. The controller 702 determines and stores first distances of movement of the table corresponding to different examination sites of a scan subject 10, wherein the different examination sites are triggered by different first trigger modes, so that the table is then moved by the corresponding first distances.

In some embodiments, for implementations of the processor 702, reference may be made to the control device 600, which will not be described here again.

In some embodiments, the medical device further includes a trigger medium. The trigger medium may be a physical key or a virtual key or a voice command received by a microphone array, specific implementations of which are as described previously, and will not be repeated here.

For example, when the trigger medium is a physical key or a virtual key, the trigger medium includes a third key 703 and a fourth key 704. The third key is provided on the table, on a magnet housing (e.g., an operation panel 706 on the housing) of the medical device, or on a control panel of an operating room. The third key is an existing function key or a combination of existing function keys of the medical device, or the third key is a newly added key of the medical device. The fourth key is provided on the table, on the magnet housing of the medical device, or on the control panel of the operating room. The fourth key is an existing function key or a combination of existing function keys of the medical device, or the fourth key is a newly added key of the medical device.

In some embodiments, when a plurality of third keys are provided, different third keys correspond to different first trigger modes. That is, by triggering corresponding third keys to enter corresponding first trigger modes, the table is triggered to be moved by the first distances, or the table is triggered to be moved by the first distances and the scanning protocols are automatically loaded. The third keys are the physical (or virtual) keys 1 and 2 in the foregoing embodiments. When one third key is provided, the different key pressing means of the third key correspond to different first trigger modes. That is, the third key is triggered by corresponding key pressing means to enter the corresponding first trigger modes, so that the table is triggered to be moved by the first distances, or the table is triggered to be moved by the first distances and the scanning protocols are automatically loaded. The third key is the physical (or virtual) key ADVANCE in the foregoing embodiments.

In some embodiments, when a plurality of fourth keys are provided, different fourth keys correspond to different second trigger modes. That is, by triggering corresponding fourth keys to enter corresponding second trigger modes, it is triggered to store the first distances or to store the first distances and the scanning protocols. The fourth keys are the physical (or virtual) keys SETA and SETB in the foregoing embodiments. When one fourth key is provided, the different key pressing means of the fourth key correspond to different second trigger modes. That is, the fourth key is triggered by corresponding key pressing means to enter the corresponding second trigger modes, so that it is triggered to store the first distances or to store the first distances and the scanning protocols. The fourth key is the physical (or virtual) key SET in the foregoing embodiments. When the first trigger modes are associated with the second trigger modes, the fourth key is combined with different third keys to then correspond to different second trigger modes. That is, by triggering the fourth key+the corresponding third keys to enter the corresponding second trigger modes, the first distances are stored, or the first distances and the scanning protocols are stored. The implementations of each trigger mode are as described previously, and will not be described again here.

Figure 8:
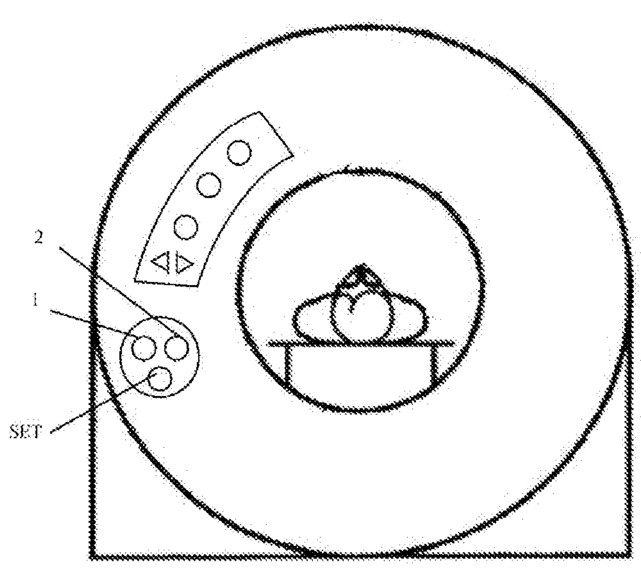
FIG. 8 is a schematic diagram of third keys and a fourth key according to an embodiment of the present application.

FIG. 8 is a schematic diagram of third keys and a fourth key according to an embodiment of the present application. As shown in FIG. 8, the third keys 1, 2 and the fourth key SET may be provided on a housing of a scanning chamber. The first distance corresponding to the examination site A is stored by pressing the keys SET+1. The table is triggered to be moved by the corresponding first distance by pressing the key 1. The first distance corresponding to the examination site B is stored by pressing the keys SET+2. The table is triggered to be moved by the corresponding first distance by pressing the key 2.

In some embodiments, when the triggering medium is a voice signal received by a microphone array, it is also necessary to mount the microphone array on the medical device, and details are as described previously. The present application is not limited thereto.

In some embodiments, the medical device may further include a first key and a second key (not shown, e.g., provided on a control panel of an operating console). The first key corresponds to an existing table movement key, and the second key corresponds to an existing advance to scan key. When the controller 702 determines the first distances, it needs to trigger the first key and the second key so that the table is moved by the corresponding second distance and third distance, the implementations of which are as described previously, and will not be described again here.

In some embodiments, the above controller 702 is connected with the table and the above various keys or microphone array, and may receive a trigger signal (a double-click signal, a click signal, a short-press signal, a long-press signal, or a voice command) of the various keys or microphone array. According to the comparison between the trigger signal and a preset program, a corresponding trigger mode is entered, a corresponding control command is generated, and the memory and table are controlled to perform corresponding operations, the details of which are as described previously, and will not be repeated here.

In some embodiments, the medical device 700 further includes a local coil 705, the details of which are as described previously, and will not be repeated here. The medical device 700 may also include a display unit (not shown), which may be used to display a user interface and various data, images, or parameters generated during data collection and processing. The above trigger medium may be virtual keys displayed on the user interface.

In some embodiments, the medical device 700 further includes an operating console (not shown), which may include a user input device such as a keyboard and a mouse. The controller 702 may communicate with other components in response to a control command generated by a user on the basis of the operating console or the control panel/keys provided on the housing of the scanning chamber or the like.

In some embodiments, the medical device 700 may further include other components or modules. For the specific content of these components or modules, reference may be made to the related technology.

In the above embodiments, by pre-storing the first distances of table movement corresponding to different examination sites and triggering the first distances corresponding to the table movement by different first trigger modes, the scanning process may be simplified, the operator does not need to repeatedly carry out a positioning operation, and the patient may be quickly and automatically positioned at the medical device scanning center, greatly increasing scan efficiency.

The embodiments of the present application further provide a computer-readable program, wherein the program, when executed, causes a computer to perform, in a medical device, the movement control method described in the foregoing embodiments.

The embodiments of the present application further provide a storage medium storing a computer-readable program, wherein the computer-readable program causes a computer to perform, in a medical device, the movement control method described in the foregoing embodiments.

The above embodiments merely provide illustrative descriptions of the embodiments of the present application. However, the present application is not limited thereto, and appropriate variations may be made on the basis of the above embodiments. For example, each of the above embodiments may be used independently, or one or more among the above embodiments may be combined.

The present application is described above with reference to specific embodiments. However, it should be clear to those skilled in the art that the foregoing description is merely illustrative and is not intended to limit the scope of protection of the present application. Various variations and modifications may be made by those skilled in the art according to the spirit and principle of the present application, and these variations and modifications also fall within the scope of the present application.

Preferred embodiments of the present application are described above with reference to the accompanying drawings. Many features and advantages of the implementations are clear according to the detailed description, and therefore the appended claims are intended to cover all these features and advantages that fall within the true spirit and scope of these implementations. In addition, as many modifications and changes could be easily conceived of by those skilled in the art, the embodiments of the present application are not limited to the illustrated and described precise structures and operations, but can encompass all appropriate modifications, changes, and equivalents that fall within the scope of the implementations.

The invention claimed is:

1. A movement control method, applied to a medical device comprising a movable table, characterized by comprising:

determining and storing first distances of movement of a table corresponding to different examination sites, wherein the movement to the different examination sites are triggered by different first trigger modes, so that the table is then moved by the corresponding first distances; and characterized in that the step of determining the first distances of movement of the table corresponding to the different examination sites comprises:

when an initial scan is performed for each examination site among the different examination sites, controlling the table to be moved by a second distance, so that a center position of a local coil of the medical device corresponding to the examination site is aligned with a positioning light of the medical device;

then controlling the table to be moved by a third distance, so that the center position of the local coil of the medical device corresponding to the examination site is aligned with a scanning center of the medical device; and determining a first distance according to the second distance and the third distance.

2. The method according to claim 1, characterized by further comprising:

when a scan is performed, triggering a first trigger mode corresponding to a site to be examined, so that the table is automatically moved by the first distance corresponding to the site to be examined.

3. The method according to claim 2, characterized by further comprising:

determining and storing the first distances of movement of the table corresponding to the different examination sites and scanning protocols corresponding to the different examination sites, wherein the first distances and the scanning protocols corresponding to the different examination sites are triggered by the different first trigger modes; and when a scan is performed, triggering the first trigger mode corresponding to the site to be examined, so that the table is automatically moved by the first distance corresponding to the site to be examined and the medical device is controlled to automatically load the scanning protocol corresponding to the site to be examined.

4. The method according to claim 1, characterized in that the different first trigger modes comprise: different physical keys, different virtual keys, different key pressing means, different voice commands, different numbers of keys, or different key combinations.

5. The method according to claim 1, characterized in that the first distances corresponding to the different examination sites are further triggered and stored by different second trigger modes.

6. The method according to claim 5, characterized in that the different second trigger modes are associated with the corresponding different first trigger modes.

7. The method according to claim 4, characterized in that the physical keys are provided on the table, on a magnet housing of the medical device, or on a control panel of an operating room.

8. The method according to claim 4, characterized in that the physical keys are existing function keys or combinations of the existing function keys of the medical device, or the physical keys are newly added keys of the medical device.

9. A medical device, characterized by comprising: a table that is movable and a controller;

the controller determining and storing first distances of movement of the table corresponding to different examination sites, wherein the movement to the different examination sites are triggered by different first trigger modes, so that the table is then moved by the corresponding first distances; and characterized in that when an initial scan is performed for each examination site among the different examination sites:

a first key of the medical device is continuously triggered until the table is moved by a second distance, so that a center position of a local coil of the medical device corresponding to the examination site is aligned with a positioning light of the medical device;

a second key of the medical device is triggered, and the table is moved by a third distance, so that the center position of the local coil of the medical device corresponding to the examination site is aligned with a scanning center of the medical device; and the controller determines a first distance according to the second distance and the third distance.

10. The medical device according to claim 9, characterized by comprising: a computed tomography device or a magnetic resonance device.

11. The medical device according to claim 9, characterized by further comprising:

a plurality of third keys, wherein different third keys correspond to different first trigger modes.

12. The medical device according to claim 11, characterized in that the first distances corresponding to the different examination sites are further triggered and stored by different second trigger modes.

13. The medical device according to claim 12, characterized by further comprising:

a fourth key, wherein the fourth key is combined with different third keys to then correspond to the different second trigger modes.

14. The medical device according to claim 11, characterized in that the third keys are provided on the table, on a magnet housing of the medical device, or on a control panel of an operating room.

15. The medical device according to claim 11, characterized in that the third keys are existing function keys or combinations of the existing function keys of the medical device, or the third keys are newly added keys of the medical device.

16. The medical device according to claim 13, characterized in that the fourth key is provided on the table, on a magnet housing of the medical device, or on a control panel of an operating room.

17. The medical device according to claim 13, characterized in that the fourth key is an existing function key or a combination of existing function keys of the medical device, or the fourth key is a newly added key of the medical device.

* * * * *